United States Patent [19]

Shene et al.

[11] Patent Number: 4,696,299
[45] Date of Patent: Sep. 29, 1987

[54] NON-INVASIVE DESTRUCTION OF KIDNEY STONES

[75] Inventors: William R. Shene, Plattsburgh, N.Y.; Christopher Nowacki, Arlington Heights; Alfred G. Brisson, Schaumburg, both of Ill.

[73] Assignee: Trutek Research, Inc., Lake Zurich, Ill.

[21] Appl. No.: 847,696

[22] Filed: Apr. 3, 1986

Related U.S. Application Data

[62] Division of Ser. No. 666,770, Oct. 31, 1984, Pat. No. 4,620,545.

[51] Int. Cl.⁴ .............................................. A61B 17/22
[52] U.S. Cl. .................................... 128/328; 128/660; 128/24 A
[58] Field of Search ..................... 128/328, 24 A, 660; 367/99, 150, 151; 73/642

[56] References Cited

U.S. PATENT DOCUMENTS

| 3,942,531 | 3/1976 | Hoff et al. | 128/328 |
| 4,311,147 | 1/1982 | Hausler | 128/328 |
| 4,539,989 | 9/1985 | Forssmann et al. | 128/328 |
| 4,610,249 | 9/1986 | Makofski et al. | 128/328 |

FOREIGN PATENT DOCUMENTS

| 0090138 | 11/1983 | European Pat. Off. |
| 2538960 | 9/1975 | Fed. Rep. of Germany |
| 3146626 | 11/1981 | Fed. Rep. of Germany |
| 3312014 | 4/1983 | Fed. Rep. of Germany |

OTHER PUBLICATIONS

Christian Chaussy, M.D., and Egbert Schmiedt, M.D., "Shock Wave Treatment for Stones in the Upper Urinary Tract", Nov. 1983, pp. 743-750.
C. Chaussy, B. Forssmann, W. Bredel, D. Jocham, F. Eisenberger, W. Hepp, J. M. Gokel, "Contact-Free Destruction of Kidney Stones by Extracorporeally Produced, Focused Shock Waves", 1980.

*Primary Examiner*—Michael H. Thaler
*Attorney, Agent, or Firm*—Robert M. Wolters

[57] ABSTRACT

Apparatus for the non-invasive disintegration of kidney stones and the like. An ellipsoidal reflector open at one end is positionable against the body, and may have a diaphragm across the opened end to prevent leakage of water contained in the reflector. A spark gap is located at the first focal point of the ellipsoid, and sonic aiming means is physically interconnected with the ellipsoid for aiming the ellipsoid at the kidney stone or the like to locate the kidney stone at the second focal point of the ellipsoid. A series of sparks discharged across the spark gap generates a succession of shock waves that travel through water in the reflector, and through the body to impinge on the kidney stone or the like and thereby to disintegrate the same.

10 Claims, 10 Drawing Figures

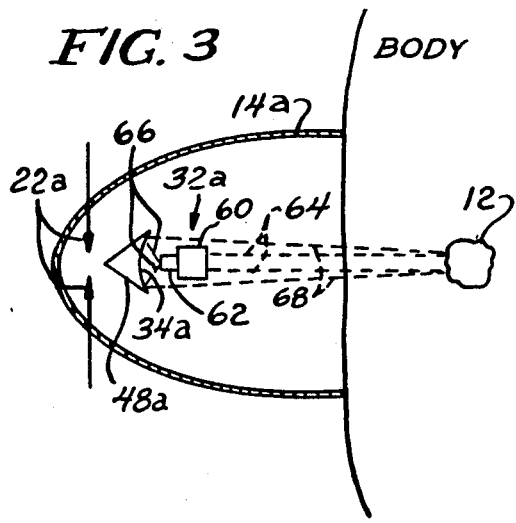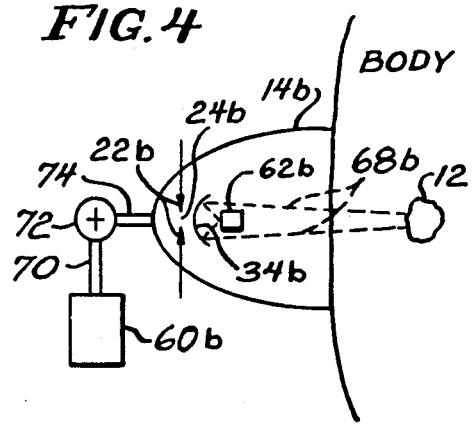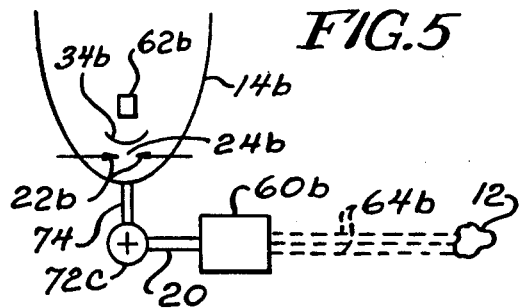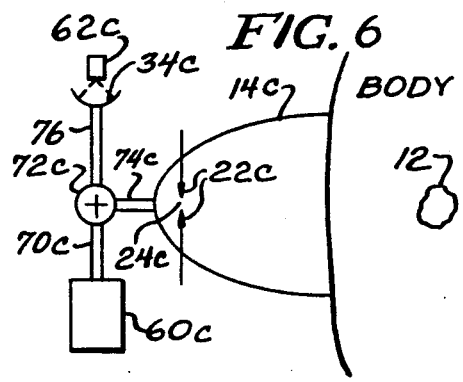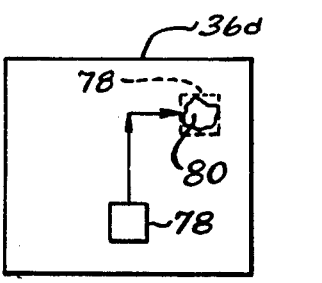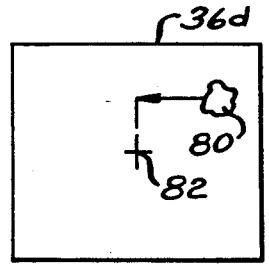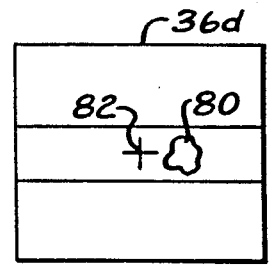

NON-INVASIVE DESTRUCTION OF KIDNEY STONES

This is a divisional of co-pending application Ser. No. 666,770 filed on Oct. 31, 1984 now U.S. Pat. No. 4,620,545.

BACKGROUND OF THE INVENTION

Kidney stones, and also naturally occuring stones in the bladder and the ureter can be exquisitely painful, and often require surgical relief. Excision or destruction of stones in the bladder and sometimes in the ureter can be relatively easily accomplished but removal of stones from the kidney is a major procedure.

Removal of stones from the kidney is a very serious and traumatic surgical procedure. A large incision is made in the body. The kidney is essentially removed from the body and cut open. The stone or stones are then removed, whereupon the kidney is sutured and returned to the body, with the body then being sutured.

Chemotherapy is available as a non-invasive therapy for uric acid stones. In this therapy the urine is alkalized. The existing stone thus is dissolved over a substantial period of time, and in most cases the patient can be cured before his condition becomes acute. However, the patient's condition is often already acute when the stone is discovered, and immediate surgery is imperative. Attempts at chemical dissolution of other types of stones have not been successful.

There are procedures for removing stones from the bladder which do not require cutting of the body. They are, however, invasive procedures in that the necessary devices are inserted through the urethra. In one of these procedures an electrohydraulic impulse is provided. A high energy capacitor is discharged by means of a coaxial electrode within the bladder, whereby a spark jumps between two poles of said electrode, establishing a hydrodynamic wave which destroys the concretion upon contact. The electrode thus must be in close proximity to the stone and a cystoscope having an optical telescope is utilized to visualize the spark generating electrodes.

As an alternative ultrasonic waves on the order of 27 KHz. are used to disintegrate bladder stones. An optical device and an ultrasound converter are carried by a hollow steel probe which is inserted through the urethra. High frequency electrical energy is transformed into mechanical energy by an ultrasound converter and carried by the hollow steel probe which must be in contact with the bladder stone.

With both electrohydraulic impulses and ultrasonic disintegration of bladder stones it has been necessary for the energy source to be very close to or to effect physical contact with the stone. Such procedures are transuretheral and are routine for bladder stones. Ureteral stones and kidney stones recently have been fragmented by such techniques percutaneously. Such procedures are invasive, but do not involve major cutting of the body.

The percutaneous approach to ureteral and kidney stones has avoided the massive surgery outlined heretofore. A needle is inserted through the skin to the renal pelvis, the collecting area of the kidney. The needle is hollow and a guide wire is inserted through the needle into the kidney. The needle is then removed, and successively larger tubes are run in over the guide wire, leading up finally to a tube 8 mm in diameter. Viewing and stone cracking apparatus then are inserted through this tube to crack or disintegrate the stone. The approach is still invasive, and traumatic to the patient.

One approach has been made on an experimental basis of non-invasive breaking-up or disintegration of kidney stones in the body. Such non-invasive disintegration of kidney stones is disclosed in U.S. Patents to Hoff et al U.S. Pat. No. 3,942,531 and Hausler U.S. Pat. No. 4,311,147. The first of these patents is exemplified in a machine commercially available in the Federal Republic of Germany from Dornier System GmbH. A few of the Dornier machines are now in the United States on an experimental basis. Such machines are quite large since they require the patient to be immersed in a tub of water in a crouched, face-up position. Two dimensional X-ray procedures are utilized to determine the position of the stone by moving the patient. The machine includes an underwater spark gap shock wave generator which lies outside of the patient's body and at the first focal point of an ellipsoid. The patient is moved around in the water bath by servo mechanisms utilizing the two dimensional X-ray technique until the kidney stone is positioned at the second focal point of the ellipsoid. Since X-rays are used only radio opaque stones can be located. The shock wave is then generated, and passes through the water bath and through the patient's body to convey the energy to the kidney stone. The Dornier machine requires a 40 square meter room 3 meters in height. The machine base is six meters by one meter. The present cost of the machine, which may be expected to rise with inflation, is two million dollars, plus 10% of the price of the machine each year for a service contract. The service contract includes the cost of a technician who must be on hand at all times when the machine is in operation. It is contra-indicated if the ureter is blocked, since the material must pass out through the ureter. It is also unsuccessful with radio transparent or translucent stones, since they cannot be located by X-ray techniques. It must be emphasized that precise aiming of an external shock wave is necessary since energy focused into an air or gas pocket in the body can cause damage to interface tissue.

OBJECTS AND SUMMARY OF THE PRESENT INVENTION

It is an object of the present invention to provide an external shock wave kidney stone disintegrator which is portable, operable by one person, and which does not require the patient's body to be immersed in a water bath.

Furthermore, it is an object of the present invention to provide an apparatus and method for external application of a hydraulic shock wave to a patient's body with the shock wave focused on the kidney stone or the like, which external aiming means is unitized with the shock wave generating apparatus to permit precise external aiming of the shock wave by a relatively simple procedure.

It is yet another object of the present invention to provide a kidney stone disintegrator as set forth in the preceding objects wherein a sonic aiming system is utilized which readily locates kidney stones which are transparent or translucent to X-rays.

In achieving the foregoing and other objects we provide an ellipsoidal reflector mechanism which is positioned against the surface of the human body. A waterproof diaphragm may be provided across the open end of the reflector to retain water in the reflector. The reflector has a spark gap positioned at the first focal point. The reflector also includes an ultrasonic or sonar transmitter and receiver which allows precise positioning of the reflector against the body so that the kidney stone will be at the second focal point of the ellipsoid. A succession of sparks is generated, causing a succession of hydraulic shock waves which pass through the water in the reflector and through the human body to the kidney stone. The energy involved is quite substantial. This succession of shocks breaks up the kidney stone, which is then excreted through the ureter, the bladder, and the urethra.

THE DRAWINGS

The present invention will be best understood from the following description when taken in connection with the accompanying drawings wherein:

FIG. 3 is a view similar to a portion of FIG. 1 showing further details on the aiming system;

FIG. 4 is a view generally similar to FIG. 3 on a somewhat reduced scale showing a modification of the aiming system;

FIG. 5 is a view similar to FIG. 4 showing the parts in a different position;

FIG. 6 is a view generally similar to FIG. 4 and showing a further modification of the aiming system;

FIG. 7 is a view similar to FIG. 6 showing the parts in a different position of operation;

FIG. 8 is a view of a modification of the CRT display utilizing imaging rather than crossed lines;

FIG. 9 is a view similar to FIG. 8 showing a different aiming condition; and

FIG. 10 is a view similar to FIGS. 8 and 9 showing yet another condition of aiming.

DETAILED DESCRIPTION OF THE ILLUSTRATED EMBODIMENT

Figure 1:
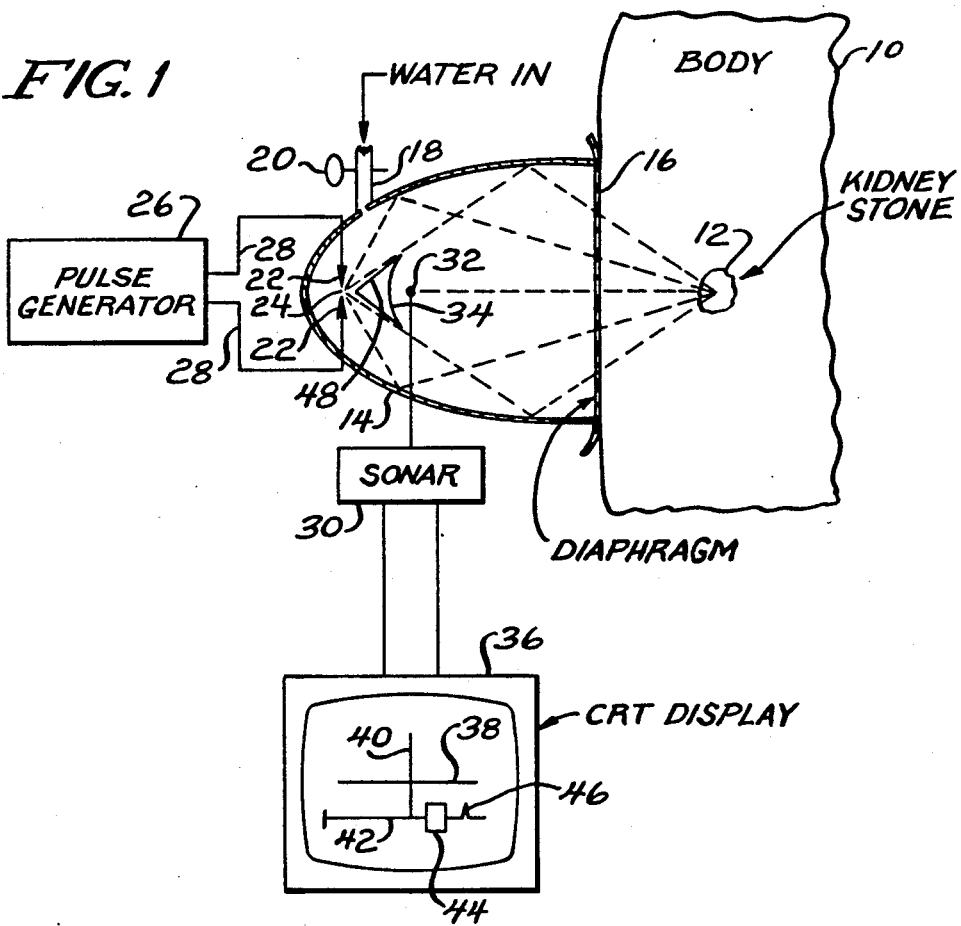
FIG. 1 is a somewhat schematic view, partially in cross-section showing an exemplification of the present invention in combination with the human body.

Turning now to the drawings in greater particularity, and first to FIG. 1, there will be seen a portion of the human body 10 illustrated somewhat schematically. The body includes a kidney stone 12. It will be understood that the present invention could be utilized equally well to remove bladder stones, but the removal of kidney stones is a more serious matter, and will be spoken of throughout.

An ellipsoidal reflector 14 is provided across its open end with a diaphragm 16 of elastomeric or plastic resin material, and is positioned against the body. The reflector is provided with a water inlet 18 having a valve 20 through which the reflector is filled with water. A pair of electrodes 22 define a spark gap 24 at the first focal point of the ellipsoid. A pulse generator 26 including a large capacitor and a voltage source is connected by means such as wires 28 to the electrodes 22.

A sonar device 30 is provided, and is powered by suitable means, not shown. The sonar device is connected to a suitable transmitting and receiving element 32 positioned in front of a reflector 34. The sonar device 30 also is connected to a cathode ray tube display 36, having horizontal and vertical lines 38 and 40 displayed thereon. The sonar device is operated, and the returning wave is compared with the timing of the output wave and controls positioning of the horizontal and vertical lines to indicate the position of the kidney stone 12.

There is a further horizontal line 42 having a box 44 thereon. A blip or pip 46 appears on the horizontal line 42 depending on the distance to the kidney stone 12 and the reflector 14, and hence the sonar transceiver 32 is moved relative to the body to cause the blip 46 to move within the box 44. This is in accordance with known sonar techniques. It will be appreciated that the human body exhibits considerable resilience, whereby the reflector 14 can be advanced or retracted relative to the body to a minor degree. For major position changes a bellows mechanism (not shown) or other extensible devices can be incorporated into the open end of the reflector.

The sonar reflector 34 may have a conical shield 48 behind it to prevent engagement by rays of the shock waved generated by the spark gap 24.

Once the reflector 14 has been properly positioned relative to the kidney stone by use of the sonar device 30 and CRT display 36 the pulse generator 26 is started in operation. This produces a series of sparks across the gap 24. Each spark causes immediate vaporization of water creating a small cavitation bubble and creating a hydraulic shock wave. The shock waves are focused by the ellipsoidal reflector and converge on the second focal point, namely the kidney stone 12. The size, the material of the kidney stone, and the manner in which it is secured together determine how much shock energy must be applied to the kidney stone to fragment it. One can estimate from a series of kidney stone disintegrations approximately how much energy is needed for a stone of a given size as shown on an X-ray. The composition cannot always be determined prior to the procedure.

When an amount of energy thought to be necessary to disintegrate the kidney stone has been delivered, then the procedure is stopped, and X-rays are taken to see if the kidney stone has been completely destroyed.

Figure 2:
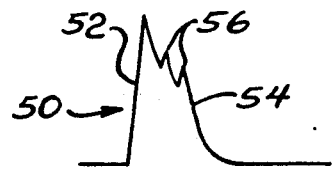
FIG. 2 illustrates the wave shape of the shock wave.

The shock wave generated has a wave shape generally similar to the electrical discharge wave of the capacitor in the pulse generator, and is shown at 50 in FIG. 2. The wave has a steep rise at 52, and a curving, slower descent 54, which may be shaped into one or more peaks 56 caused by the changing of the spark gap upon sparking and the conical shield 48.

The sonar device transmitting and receiving element 32 has been shown in the ideal situation as being quite small. However, for an imaging type readout it is necessary to provide both a non-focused transducer and a focused transducer. This structure is illustrated schematically in FIG. 3 in which the focused transducer is illustrated at 60 and the non-focused transducer is illustrated at 62. The focused transducer 60 sends and receives a focused ultrasonic beam 64 to and from the kidney stone 12. The focused transducer is generally used for locating the direction of the stone. The non-focused transducer 62 sends a non-focused ultrasonic wave 66 rearwardly against the reflector 34a (similar parts in FIG. 3 being identified by similar numerals with the addition of the suffix a) from whence it is reflected at 68 to engage the kidney stone 12 and to reflect back to the reflector 34a and to the non-focused transducer. The non-focused transducer is used for determining the distance to the target.

For simplicity of illustration in FIG. 3 supports for the transducers and for the reflector and conical shield, and the water inlet have been omitted. The same is true also in FIGS. 4–7.

The non-focused transducer is relatively small, and under most circumstances can be placed in the reflector. However, the focused transducer is larger, and in some cases it may get in the way of the waves from the non-focused transducer, or it may get in the way of the hydraulic shock wave. To accommodate to this condition a modification of the invention is provided as shown in FIGS. 4 and 5, wherein similar parts are identified by the use of similar numerals with the addition of the suffix b. In this case, the focused transducer 60b is disposed externally of the reflector 14b, and it is connected by a rigid support member 70 to a pivot 72. The reflector 14b is also connected by a rigid support member 74 to the pivot 72. In the specific example the axes of the reflector 14b and of the focused transducer 60b are disposed at right angles. The pivot member 72 is of the locking type, and the parts may be positioned as in FIG. 4 with the reflector 14b in position for use of the non-focused transducer 62b or for use in the hydraulic shock wave, or the parts may be pivoted 90 degrees to the position shown in FIG. 5 for use of the focused transducer 60b. The lengths of the support members 70 and 74 are correlated so as to maintain the focused transducer 60b and the reflector 14b, and particularly the focal point of the spark gap electrodes 22b in proper correlation relative to the kidney stone 12. It will be understood that the pivot member 72 is itself pivotally supported, or comprises a swivel, for pivoting movement perpendicular to the plane of the drawing to accommodate for the third dimension necessary to aim at the kidney stone. This latter pivotal swivel may be omitted with other provision made for relative lateral positioning of the reflector 14b and of the kidney stone 12. This may be done by physically shifting the reflector 12b, or by shifting the body bearing the kidney stone 12.

In still other instances it may be desired to position a non-focused transducer outside of the reflector. Such a modification is shown in FIGS. 6 and 7 wherein like parts are identified by similar numerals with the addition of the suffix c. In this embodiment the focused transducer 60c is again positioned at right angles to the reflector 14c, these parts respectively being supported on support elements 70c and 74c from the pivot 72c. In this instance the non-focused transducer 62c is supported by support means such as a plurality of wires or rods (not shown) from the reflector 34c, which is in turn supported by support member 76 from the pivot member 72c. Although both transducers are illustrated as being supported at 90 degrees relative to the reflector 14c, it is apparent that other angles could be used. The pivot member 72c is pivotable 90 degrees in one direction to bring the focused transducer 60c into position for operation with the kidney stone 12, just as in FIG. 5, and the pivot 72c may be pivoted in the opposite direction as shown in FIG. 7 to bring the non-focused transducer 62c into position for operation with the kidney stone 12.

As noted earlier a CRT (cathode ray tube) display may utilize cross lines and align cross lines from the target kidney stone with base lines on the CRT. This is a known technique, and in most cases is expected to be satisfactory. However, there is an ultrasonic imaging technique which may be preferred over the cross lines in many instances. Such imaging is illustrated in FIG. 8, in which the CRT display includes a box 78, the position of which is controlled on the screen by the operator. The image area of interest contained by the box is then expanded to fill the full screen as in FIG. 9. Simultaneously, cross hairs 82 are generated in the center of the screen, and the focusing transducer is further oriented to move the image 80 of the stone into position centered on the cross hairs.

The upper and lower portions of the screen then are blanked out to leave only an active center portion 82, and the non-focused transducer then is brought into play to produce an image 80 of the kidney stone which is moved by positioning the non-focused transducer into a position of alignment with the cross hairs 82 which is used to determine the position of the target kidney stone. When the image of the kidney stone is centered on the cross hairs, then the non-focused transducer is at the proper location from the kidney stone so that the reflector 14c can be pivoted into position to have the spark gap 24c and the kidney stone lie on the two focus points of the elipsoidal reflector.

In each embodiment of the present invention the critical factor is that the ultrasonic aiming means is physically interconnected with the elipsoidal reflector so that the reflector can be positioned relative to the body to place the kidney stone at one focus point of the elipsoid, the spark gap creating the hydraulic shock wave being at the other focus point. This can be effected by having an ultrasonic transducer within the elipsoidal reflector and movable with the reflector, or it can be effected by having one or more ultrasonic transducers outside of the reflector, and one or none within the reflector, but bearing predetermined relation to the reflector so that the reflector is ultimately positioned in accordance with the positioning of the ultrasonic transducer(s).

The specific examples of the invention as herein shown and described are for illustrative purposes only. Various changes in structure will no doubt occur to those skilled in the art, and will be understood as forming a part of the present invention insofar as they fall within the spirit and scope of the appended claims.

The invention is claimed as follows:

1. Apparatus for the non-invasive disintegration of concretions such as kidney stones within a living body, comprising means including a focussing reflector comprising a portion of an ellipsoid open at one end and having a first focus point within said reflector and having a second focus point outside of said reflector positioned beyond said open end, said first and second focus points lying on the focal axis of said reflector, said reflector being adapted to contain a fluid such as water, a fluid retaining diaphragm closing said open end and engagable with said body, sonic aiming means disposed entirely exteriorly of said reflector and positioned relative to said reflector to permit said sonic aiming means to focus on said concretion exteriorly of and free of obstruction by said reflector, said sonic aiming means having a focussing direction displaced from and non-intersecting with said reflector focal axis, said reflector being interconnected with and movable with said sonic aiming means focus to bring said second focus point into coincidence with said concretion with concurrent movement of said sonic aiming means away from said concretion, and spark gap means in said reflector at said first focus point for generating a shock wave which will travel through said fluid, said diaphram and through said body to disintegrate said concretion.

2. Apparatus as set forth in claim 1 wherein said sonic aiming means is physically connected to said reflector.

3. Apparatus as set forth in claim 2 wherein said sonic aiming means is fixed relative to said reflector.

4. Apparatus as set forth in claim 3 and further including means pivotally mounting said reflector.

5. Apparatus as set forth in claim 3 wherein said reflector has a major axis, and wherein said sonic aiming means is disposed at a predetermined angle relative to said major axis.

6. Apparatus as set forth in claim 5 wherein said sonic aiming means comprises a focused sonic transducer and a non-focused sonic transducer.

7. Apparatus as set forth in claim 6 wherein said focused sonic transducer and said non-focused sonic transducer respectively lie on opposite sides of said reflector's major axis.

8. Apparatus as set forth in claim 7 and further including means pivotally mounting said reflector, said focused sonic transducer and said non-focused sonic transducer being aligned with one another and aimed in opposite directions away from one another.

9. Apparatus as set forth in claim 3 wherein said sonic aiming means comprises a focused sonic transducer and a non-focused sonic transducer.

10. Apparatus as set forth in claim 9 wherein said focused sonic transducer and said non-focused sonic transducer are respectively located at two different positions.

* * * * *